(12) United States Patent
Lowin

(10) Patent No.: US 10,518,099 B2
(45) Date of Patent: Dec. 31, 2019

(54) TRANSCRANIAL MAGNETIC STIMULATION SYSTEM AND METHODS

(71) Applicant: Seraya Medical Systems LLC, Greenwich, CT (US)

(72) Inventor: Leeam Lowin, Greenwich, CT (US)

(73) Assignee: SERAYA MEDICAL SYSTEMS LLC, Greenwich, CT (US)

(*) Notice: Subject to any disclaimer, the term of this patent is extended or adjusted under 35 U.S.C. 154(b) by 0 days.

(21) Appl. No.: 16/033,541

(22) Filed: Jul. 12, 2018

(65) Prior Publication Data

US 2019/0015674 A1 Jan. 17, 2019

Related U.S. Application Data

(63) Continuation of application No. 15/634,329, filed on Jun. 27, 2017, now Pat. No. 10,046,171, which is a continuation of application No. 15/243,669, filed on Aug. 22, 2016, now Pat. No. 9,782,602.

(60) Provisional application No. 62/355,209, filed on Jun. 27, 2016.

(51) Int. Cl.
*A61N 2/00* (2006.01)
*G01K 13/00* (2006.01)
*G01K 7/36* (2006.01)
*A61N 2/02* (2006.01)
*A61N 2/06* (2006.01)

(52) U.S. Cl.
CPC ............ *A61N 2/006* (2013.01); *A61N 2/008* (2013.01); *A61N 2/02* (2013.01); *A61N 2/06* (2013.01); *G01K 7/36* (2013.01); *G01K 13/00* (2013.01)

(58) Field of Classification Search
CPC .......... A61N 2/006; A61N 2/02; A61N 2/008; A61N 2/06; G01K 13/00; G01K 7/36
See application file for complete search history.

(56) References Cited

U.S. PATENT DOCUMENTS

| 6,447,440 B1 | 9/2002 | Markoll |
| 8,560,073 B2 | 10/2013 | Osorio |
| 2011/0015469 A1 | 1/2011 | Wlater |

(Continued)

OTHER PUBLICATIONS

International Search Report and Written Opinion in corresponding PCT Application No. PCT/US 17/39521, dated Sep. 29, 2017.

*Primary Examiner* — Christine H Matthews
*Assistant Examiner* — Joshua Daryl D Lannu
(74) *Attorney, Agent, or Firm* — Leason Ellis LLP

(57) ABSTRACT

A transcranial magnetic stimulation device in accordance with embodiments of the present invention comprises a head mount for disposition on a head of a patient and configured with a plurality of attachment points, a plurality of magnetic assembly devices connected to the plurality of attachment points, a given magnetic assembly device equipped with an actuator device to actuate a magnet, is addressable, and configured to receive a control signal addressed to the given magnetic assembly device, and a processor having a memory and configured by program code. The processor is configured to: select one or more treatment protocol units, generate a control signal using at least information contained in the selected treatment protocol units, energize at least one magnetic assembly device over a period of time to cause the magnet to actuate according to the control signal, and monitor the patient response to energizing the at least one magnetic assembly device.

19 Claims, 8 Drawing Sheets

(56) References Cited

U.S. PATENT DOCUMENTS

2011/0034822 A1    2/2011   Phillips et al.
2012/0053449 A1    3/2012   Moses
2014/0276182 A1*  9/2014   Helekar ............... A61B 5/6803
                                                        600/544

* cited by examiner ic Stroke using a New Wearable Multifocal Brain Stimulator", MORTI—Methodist Online Research Technology Initiative, Date Entered State: Apr. 20, 2016; and
TRANSCRANIAL MAGNETIC STIMULATION SYSTEM AND METHODS

CROSS-REFERENCE TO RELATED APPLICATIONS

This is a continuation of U.S. Ser. No. 15/634,329, filed Jun. 27, 2017, which is a continuation of U.S. application Ser. No. 15/243,669, filed Aug. 22, 2016, which is now a U.S. Pat. No. 9,782,602, issued Oct. 10, 2017 and claims the benefit of priority under 35 U.S.C. Section 119(e) of U.S. Application Ser. No. 62/355,209, filed Jun. 27, 2016, which are hereby incorporated by reference in their respective entireties.

FIELD OF THE INVENTION

The present invention is directed to systems that implement Transcranial Magnetic Stimulation and methods of use thereof. In particular, embodiments of the invention relate to energizing one or more magnetic assembly devices, which may comprise energizing sets of magnetic assembly devices in parallel or serial, that are in proximity of the cranium of a patient such that energizing causes the generation of an electrical field within the brain of the patient. A treatment protocol unit comprises program code that identifies a plurality of operating parameters of a given magnetic assembly device and, when interpreted by a programmable processor, instruct the processor as to manner and timing of such energizing. A plurality of treatment protocol units can be grouped for processing and stored as a treatment protocol to allow for the reproducible treatment of a given illness.

BACKGROUND OF THE INVENTION

Transcranial Magnetic Stimulation ("TMS") is a non-invasive procedure in which magnetic stimulation is applied to the brain to modify the natural electrical activity of the brain, to provide therapy to a patient, to assist in diagnosis, to map out brain function in neuroscience research or implement any other technique where it might be advantageous to modify the natural electrical activity of the brain. More particularly, certain TMS techniques apply a rapidly changing magnetic field to the brain of a patient to induce weak electric currents in the brain of the patient by way of electromagnetic induction. TMS has been approved by the U.S. Food and Drug Administration ("FDA") for treating depression. TMS is also currently being investigated in the management of various other neurological and psychiatric disorders including, but not limited to, migraines, aphasia, anxiety, Parkinson's disease, tinnitus, autism, schizophrenia, Alzheimer's, ALS, stroke (e.g., ischemic), Myotonic Dystrophy type 1 ("DM1"), stuttering, epilepsy, visceral pain and dystonia, as well as cocaine, opioid and other addictive behavior.

Researchers in the field of TMS are increasingly uncovering ailments and conditions that can be managed or ameliorated through the use of TMS devices. For example, the following non-exhaustive list of scholarly literature details the use of TMS to treat various ailments, all of which are hereby incorporated by reference as it set forth in its entirety herein:

Rosenfield, David, et al., "Neuromodulation by Paired Associative Brain Magnetic Stimulation of Speech Areas in Stuttering", MORTI—Methodist Online Research Technology Initiative, Date Entered State: Feb. 12, 2015;

Simpson, Ericka, et al., "A pilot study of repetitive multisite transcranial magnetic stimulation with wearable device in Myotonic Dystrophy type 1", MORTI—Methodist Online Research Technology Initiative, Date Entered State: Nov. 10, 2014;

Appel, Stanley, et al., "Focal Magnetic Stimulation of the Motor Cortex to Induce Motor Evoked Potentials for Diagnostic Evaluation in Amyotrophic Lateral Sclerosis", MORTI—Methodist Online Research Technology Initiative, Date Entered State: Sep. 30, 2013;

Appel, Stanley, et al., "Focal Magnetic Stimulation of the Motor Cortex to Induce Motor-Evoked Potentials for Diagnostic Evaluation in Amyotrophic Lateral Sclerosis", MORTI—The Methodist Hospital Research Institute, Study Approval: Sep. 24, 2015;

Chiu, David, et al., "Multifocal brain magnetic stimulation in chronic ischemic stroke. An Innovative Approach to Restoration of Function in Chronic Ischemic Stroke using a New Wearable Multifocal Brain Stimulator", MORTI—Methodist Online Research Technology Initiative, Date Entered State: Apr. 20, 2016; and Chiu, David, et al., "An Innovative Approach to Restoration of Function in Chronic Ischemic Stroke using a New Wearable Multifocal Brain Stimulator", MORTI—Methodist Online Research Technology Initiative, Consent Approval Date: Mar. 30, 2016.

Furthermore, Theta Burst Stimulation (TBS), a high-frequency variant of TMS has been shown to induce prolonged plasticity changes in the brain. The induction of plasticity-like effects by TBS is useful in both experimental and therapeutic settings.

U.S. patent application Ser. No. 13/829,349, published as U.S. Patent Publication No. 2014/0276182, hereby incorporated by reference as if set forth in its entirety herein, describes TMS apparatus as generally comprising an electromagnetic coil that is in a fixed position relative to the head of the patient. Since the magnetic field applied to the patient is a function of the configuration of the electromagnetic coil, the current passed through the electromagnetic coil, and the location of the electromagnetic coil relative to the patient, the fixed construction of such a TMS apparatus significantly limits the character of the magnetic field that can be applied to the patient, and, accordingly, the TMS therapies that can be provided to the patient. In addition, such TMS apparatuses generally utilize very high electrical currents in the electromagnetic coil, which raises the risk of accidental injury to the patient through electric shocks, burns, seizures, etc.

In the art there exists a need to have both standardized and customizable libraries of patterns of magnetically induced current within the brain of a patient for particular treatments. Currently available TMS devices generally follow set routines for determining which of a plurality of magnets arranged on a cap or helmet are used to induce electric fields. Determining which magnet or magnets to use to induce electric fields, as well as the corresponding operational parameters, is often left to researchers or practitioners. Thus, reproducible and improved results are only achievable by codifying the various operational parameters that influence the electric fields induced in the brain of a user as part of any given therapy.

What is therefore needed in the art are systems, methods and computer program products for inducing electric currents within the brain of a subject using TMS treatments while minimizing the potential for negative side effects due to high current electromagnets. Furthermore, what is needed is a library of standardized and customizable treatment protocol units that can be used to build a treatment protocol that is customizable to the specific user, ailment, diagnostic technique or various combinations thereof.

SUMMARY OF THE INVENTION

Embodiments of the invention are directed towards systems, methods and computer program products for transcranial magnetic stimulation system using magnetic assembly devices that variably energize and, when energized, create one or more electrical fields within the brain of a patient. In one embodiment, the present invention is directed to a transcranial magnetic stimulation system comprising a plurality of addressable magnetic assembly devices each connected to a respective plurality of attachment points on a cap intended to be worn on the head of a patient. A given magnetic assembly device is equipped with an actuator device to actuate a magnet, which may comprise rotation of a permanent magnet, the actuation device configured in certain embodiments to rotate the magnet at one of a plurality of frequencies.

A given one of the magnetic assembly devices is configured to receive a control signal addressed to the actuator and monitor, through one or more sensors, one or more operating parameters associated with the a given magnetic assembly device. Furthermore, the system utilizes a processor having a memory and being configured by code executed thereby to: select at least one treatment protocol unit for inclusion in a treatment protocol that applies a therapeutic or diagnostic treatment, wherein a given treatment protocol unit comprises at least data corresponding to a rotational frequency; generate a control signal using at least information contained in the selected treatment protocol units and energize at least one magnetic device assembly over a period of time to rotate according to the control signal. The program code further instructs the processor as to monitoring the patient in response to application of a given treatment protocol unit.

In another embodiment, the present invention is directed to a method for transcranial magnetic stimulation that comprises providing a head mount for disposition on the head of a patient. The head mount comprises a plurality of points for releasable mounting a plurality of magnetic device assemblies, a given magnetic device assembly comprising a magnet and an actuator device for selectively providing a rapidly changing magnetic field capable of inducing weak electric currents in the brain of a patient so as to apply a treatment that modifies the natural electrical activity of the brain of the patient. The head mount is positioned on the head of the patient in conjunction with a selected number of magnet assemblies supported on the head mount at selected locations. The method continues with the selection of one or more treatment protocol units for assembly into a treatment protocol for execution by a programmable processor, the programmable processor operative to generate one or more control signals for respective magnetic device assemblies on the basis of the treatment protocol units. A rapidly changing magnetic field is provided by at least one of the magnet assemblies in accordance with the treatment protocol and in response to receipt of a respective control signal.

BRIEF DESCRIPTION OF THE DRAWINGS

Embodiments of the invention are illustrated in the figures of the accompanying drawings which are meant to be exemplary and not limiting, in which like references are intended to refer to like or corresponding parts, and in which.

DETAILED DESCRIPTION OF CERTAIN EMBODIMENTS OF THE INVENTION

By way of overview, various embodiments of the systems, methods and computer program products described herein are directed towards a transcranial magnetic stimulation device that is configurable through the use of one or more treatment protocol units that an operator or software process selects from a library of treatment protocol units. A collection of one or more treatment protocol units define a treatment protocol for execution by a programmable processor as a set of computer program instructions, which causes one or more actuator devices to rotate one or more magnets to induce varying electric fields within the brain of the patient. As used herein, a patient is any person that interacts with the transcranial magnetic stimulation device, either through operation or application, and which may include at least interaction for diagnostic, therapeutic or mapping purposes. A patient self-directing the system described is referred to as a patient or, alternatively, as a user. Likewise, a person directing the system worn by another is also indicated as a user or a clinician, as used herein.

Figure 1:
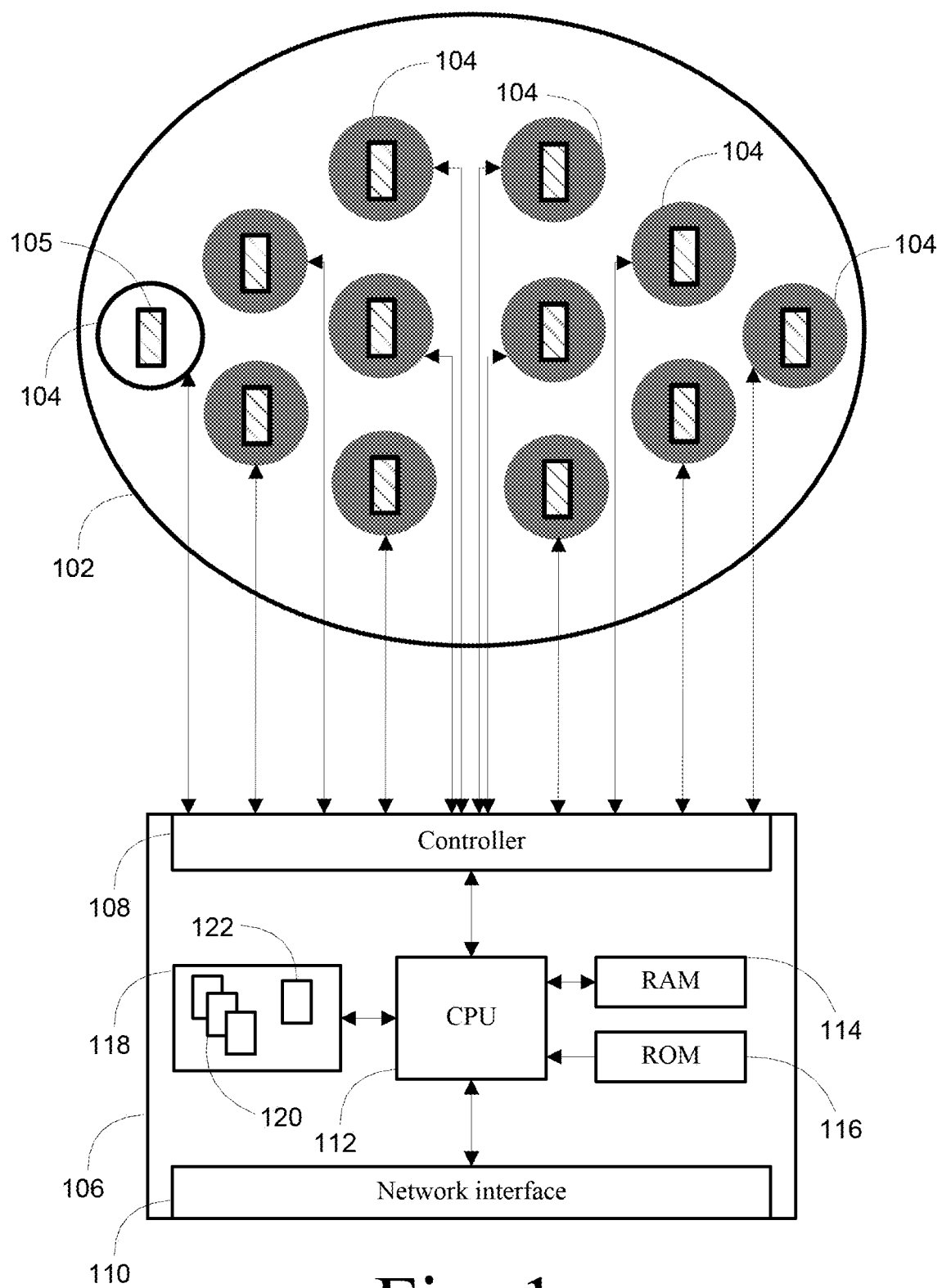
FIG. 1 illustrates a block diagram of a system for transcranial magnetic stimulation according to one embodiment of the present invention.

With particular reference to FIG. 1, the transcranial magnetic system comprises a harness, frame or cap 102 that may be secured to the head of a patient (not shown). The cap 102 is configured with a plurality of attachment points where one or more magnetic assembly devices 104 can be permanently connected. Alternatively, or in conjunction with the foregoing, one or more magnetic assembly devices 104 may be detachably affixed to the cap 102. In one configuration, therefore, attachment points may be predetermined, such as through the use of snaps, buttons, fasteners or other fixed attachment points that permit the releasable attachment of the magnetic assembly devices 102 to the cap at specific points thereon. Instead of or in conjunction with the foregoing, the cap can be equipped with rails, channels or similar structures containing conductive elements that enable a given magnetic assembly device 104 to be variably secured at any point along the channel or rail, depending on the desired treatment location or the cranial structure of a given patient. The attachment points can all be of like design to permit a standard magnetic assembly device to be attached anywhere along the cap 102, or the attachment points can provide more than one fitting to mate with particular, corresponding magnetic assembly devices.

In accordance with the embodiment that FIG. 1 illustrates, the attachment points are positioned on the cap 102 at locations corresponding to specific areas of the brain of a given user, thereby optimizing the delivery of magnetic energy for a given diagnosis, therapy, mapping, or other application of the present invention. It will be appreciated by those possessing an ordinary level of skill in the requisite art, however, that other configurations of the magnetic assembly devices 104 are possible on the basis of the underling application or desired result.

Figure 2:
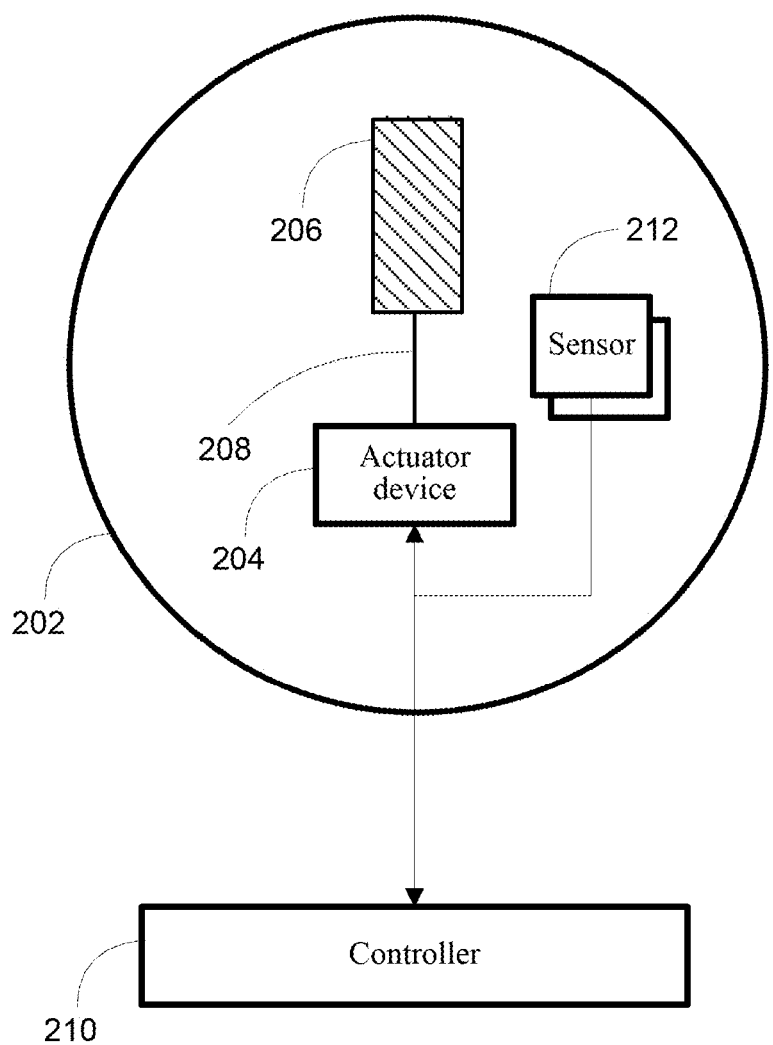
FIG. 2 presents a block diagram illustrating a magnetic assembly device according to one embodiment of the present invention.

A given magnetic assembly device 104 that may be affixed to the cap 102 comprises an actuator device (not shown) and a magnet 105. FIG. 2 provides a more detailed illustration of an exemplary magnetic assembly device 104 (now labeled 202, but in all respects can be the same device) in which the actuator device 204 is a motor configured to rotate a magnet 206 in response to control signals that the actuator device 204 receives via a controller 210. In one or more configurations, the actuator device 204 is a stepper motor. In an alternative arrangement, however, the actuator device 204 is a brushed motor. Other actuator device types known to those of skill in the art can further be utilized by certain embodiments. In accordance with various embodiments of the magnetic assembly device 202 shown in FIG. 2, the actuator device 204 is a variable speed motor, such that the magnet 206 may be rotated faster or slower as desired or needed by a given treatment protocol, which is explained in greater detail herein.

In accordance with various embodiments of the system of the present invention, a number of disparate types of magnets may be used. In one embodiment of the magnetic assembly device 202, the magnet 206 is an electromagnet. In alternative embodiments, however, the magnet is a permanent magnet. In accordance with a system utilizing one or more permanent magnets, such permanent magnet is a rare earth, or natural magnet, e.g., a neodymium magnet. In an alternative arrangement, the magnet 206 is a soft magnetic composite ("SMC") magnet.

The magnet 206 is affixed to a rotator shaft 208 in communication with the actuator device 204, such that when the actuator device 204 is energized, the magnet 206 rotates about an axis. Rotating the magnet 206 creates a rapidly changing magnetic field about the magnetic assembly device 202. In one embodiment of the invention, each of the magnet assembly devices comprises a permanent magnet for selectively providing a rapidly changing magnetic field of at least 500-600 Tesla/second and corresponding to a magnet movement speed of no less than 400 Hertz. As will be appreciated by those knowledgeable in the field of TMS, weak electric current is induced in neurons within the brain of a patient through the application of a rapidly changing magnetic field of at least 500-600 Tesla/second and corresponding to magnet movement speed of no less than 400 Hertz. These weak electric currents modify the natural electrical activity of the brain of the patient to provide the patient with targeted therapies, to assist in diagnosis or to map out brain function for use in neuroscience research.

In one exemplary configuration of the magnetic assembly device 204, the actuator device 204 may comprise both a motor for rotating the magnet and a lateral movement device (not pictured) for changing the position of the magnet relative to the patient, such as solenoid. In this exemplary configuration, the lateral movement device in the magnetic assembly device 202 positions the magnet 206 closer or further away from brain of the patient, which may be dependent upon particular treatment parameters that a user is applying to the patient. The lateral movement device optionally enables azimuth adjustment in addition to or as the lateral movement.

In a further arrangement, the magnetic assembly device 202 comprises one or more sensors 212 used to monitor the magnetic field, temperature of the assembly device, the current induced in the brain, or other data points regarding the patient that the sensor may collect. Such data can comprise biophysical data as is known to those of skill in the art. In one arrangement, the sensors 212 comprise an array of one or more electrodes that are configured to measure electrical activity of the brain and send the measured data as a signal back to the controller 210.

As the embodiment of FIG. 2 illustrates, one or more sensors 212 deployed as part of the magnetic assembly device 202 collect information with respect to the operational conditions of the device 202, such as measuring magnetic fields, current induced and temperature. The sensor(s) 212 can pass the gathered information back to the control device via a return channel from the magnetic assembly device 202 to the controller 210. According to one embodiment, the sensor(s) 212 pass the gathered information back to the control device in real-time. In this embodiment, the processor at the control device receives the operational parameters from the sensor(s) 212 and activates or deactivates one or more of the magnetic assembly devices 202, e.g., upon detection of conditions that exceed safety or comfort thresholds, or in response to feedback regarding desired output levels.

The data gathered can be packaged and uploaded to a persistent data store, which may be local or remote to the control device, e.g., to serve as supporting data with regard to the safety or efficacy of a particular treatment protocol unit or treatment protocol. The collected information on the efficacy of a particular treatment protocol or individual treatment protocol units can be collected and sent to a persistent data store for access and evaluation by third parties. For example, researchers accessing such collected information are thus able to test and validate individual treatment protocol units and treatment protocols, both of which are described in detail herein, as well as make alterations or modifications thereto. Such modifications can be directed to improvements in treating a particular ailment or repurposing a treatment protocol unit or treatment protocol to address a different ailment or condition.

Turning back to the exemplary embodiment that system that FIG. 1 illustrates, a given one of the magnetic assembly devices 104 may be directly connected to the control device 106. In accordance with one embodiment, a given one of the magnetic assembly devices 104 is connected to a controller 108 that is part of the control device 106, which can be the same as controller 210 mentioned above. The controller 108 is under the direction and control of a processor 112 that instructs the controller 108 to selectively deliver control signals to one or more of the magnetic assembly devices 104, thereby causing the magnet 105 that forms a component of a given magnetic assembly device 104 to rotate. As is described in greater detail herein, rotation of magnet 105 by an actuator device is effected by the controller 108 in accordance with the specific instructions that the controller 108 receives from the processor 112.

The controller 108 communicates with one or more of the magnetic assembly devices 104 through a physical link, a wireless link or combinations thereof. As shown in exemplary embodiment of FIG. 1, the controller communicates with the magnetic assembly devices 104 using single communication links, one for each magnetic assembly device 104. In certain configurations, however, the controller 108 communicates with the magnetic assembly devices 104 through the use of various combinations of one or more conduits, USB, serial, or wired or wireless communication links that are known to those of ordinary skill in the art.

In the provided example, the controller 108 may comprise a discrete processor, gate array, logic switch or other device configurable to selectively energize one or more magnet assembly devices 104 in response to an instruction set or command signal, which the control device 106 may receive from an operator or automated software process. For instance, the controller 108 may be a processor configured with hardware and/or software switches to control the activation state and rotation of the magnetic assembly devices 104, access activation state data regarding of one or more connected magnetic assembly devices, as well as provide additional instructions to and collect any incoming data from a given magnetic assembly device 104. The controller 108 comprises one or more mechanisms, such as specified or listed ports, for identifying and selecting one or more specific magnetic assembly devices 104. Accordingly, since connections between the controller 108 and the magnetic assembly device 104 are known and identified, the control device 106 provides for individual control of specific magnetic assembly devices 104.

Where a controller 108 is present and connected to the magnetic assembly devices 104, the activation of one or more of the magnetic assembly devices 104 are operated in response to a set of one or more control instructions or signals passed by the controller 104 from a computer or processor 112. In one implementation, the controller 108 has a physical connection to the processor 106. In an alternative configuration whereby the processor 112 is housed in a device or assembly that is external to the controller 108, the controller 108 and processor 112 are equipped with bi-directional communication hardware and software protocols to allow for data to be exchanged by and between the controller 108 and the processor 112.

The control device 106 according to one embodiment of the present invention is a desktop or workstation class computer that executes a commercially available operating system, e.g., MICROSOFT WINDOWS, APPLE OSX, UNIX or Linux based operating system implementations. In accordance with further embodiments, the control device 106 is a portable computing device such as a smartphone, wearable or tablet class device. For example, the control 106 is an APPLE IPAD/IPHONE mobile device, ANDROID mobile device or other commercially available mobile electronic device configured to carry out the processes described herein. In other embodiments, the control device 106 comprises custom or non-standard hardware configurations. For instance, the control device 106 may comprise one or more micro-computer(s) operating alone or in concert within a collection of such devices, network adaptors and interfaces(s) operating in a distributed, but cooperative, manner, or array of other micro-computing elements, computer-on-chip(s), prototyping devices, "hobby" computing elements, home entertainment consoles and/or other hardware.

The control device 106 can be equipped or is in communication with a persistent storage device 118 that is operative to store the operating system in addition to one or more of software modules 122, such as those described herein to implement transcranial magnetic stimulation in accordance with embodiments of the present invention. In one embodiment of the present invention, the modules utilized by the control device 106 comprise software program code 122 and data 120 that are executed or otherwise used by the processor 112 comprising the control device 106 (e.g., executed code), thereby causing the control device 106 to perform various actions dictated by the software code of the various modules 122. In accordance with certain embodiments, the control device 106 is in communication with a persistent data store 118 that is located remote from the control device 106 such that the control device 106 access the remote persistent data store over a computer network, e.g., the Internet, via a network interface 110, which implements communication frameworks and protocols that are well known to those of skill in the art.

In addition to a persistent storage device 118, the control device 106 may comprise primary computer memories, such as a read only memory (ROM) 116 and/or a random access memory (e.g., a RAM) 114. The computer memories may also comprise secondary computer memory, such as magnetic or optical disk drives or flash memory, that provide long term storage of data in a manner similar to the persistent storage device 118. In accordance with one or more embodiments, the memory comprises one or more volatile and non-volatile memories, such as Programmable Read Only-Memory ("PROM"), Erasable Programmable Read-Only Memory ("EPROM"), Electrically Erasable Programmable Read-Only Memory ("EEPROM"), Phase Change Memory ("PCM"), Single In-line Memory ("SIMM"), Dual In-line Memory ("DIMM") or other memory types. Such memories can be fixed or removable, as is known to those of ordinary skill in the art, such as through the use of removable media cards or similar hardware modules. In one or more embodiments, the memory of the control device 106 provides for storage of application program and data files when needed by the processor 112. One or more read-only memories 116 provide program code that the processor 112 reads and implements at startup or initialization, which may instruct the processor 112 as to specific program code from the persistent storage device 118 to load into RAM 114 at startup.

Certain embodiments contemplate deploying the persistent data store 118 as a database that is connected to the control device 106 and contains at least transcranial magnetic stimulation application program code 122 and a library of treatment protocol units 120 for execution by the processor 112 in governing the operational parameters of the magnetic assembly devices 102. The treatment protocol units are, in one arrangement, data objects detailing specific operational characteristics that are implementable by the magnetic assembly devices 104. As is described in greater detail herein, one or more treatment protocol units may be sequentially combined to form a treatment protocol.

In one configuration, the database 118 is connected to the control device 106 via a server or network interface 110 and provides additional storage or access to user data, community data, or general purpose files or information. The physical structure of the database 118 may be embodied as solid-state memory (e.g., ROM), hard disk drive systems, RAID, disk arrays, storage area networks ("SAN"), network attached storage ("NAS") and/or any other suitable system for storing computer data. In addition, the database 118 may comprise caches, including database caches and/or web caches. Programmatically, the database 118 may comprise flat-file data store, a relational database, an object-oriented database, a hybrid relational-object database, a key-value data store such as HADOOP or MONGODB, in addition to other systems for the structure and retrieval of data that are well known to those of skill in the art.

Building on the prior example, the control device 106 at startup retrieves initial instructions from ROM 116 as to initialization of the processor 112. Upon initialization, program code that the processor 112 retrieves and executes from ROM 116 instructs the processor to retrieve and begin execution of transcranial magnetic stimulation application program code 122. The processor begins execution of the transcranial magnetic stimulation application program code 122, loading appropriate program code to run into RAM 114 and presents a user interface to the user that provides access to one or more functions that the program code 122 offers. According to one embodiment, the transcranial magnetic stimulation application program code 122 presents a main menu after initialization that allows for the creation or modification of treatment protocol units and treatment protocols, as well as the application or one or more treatment protocols to a user. While reference is made to code executing in the processor, it should be understood that the code can be executed or interpreted or comprise scripts that are used by the processor to implement prescribed routines.

When a user desires to create one or more treatment protocol units, he or she may access functionality that the transcranial magnetic stimulation application program code 122 provides to instantiate a data structure that represents such treatment protocol units 120. As is described in greater detail herein, the operational parameters of a given treatment protocol unit 120 comprise a series of key-value pairs that user defines and which control operation of one or more magnetic assembly devices. Similarly, when the user desires to modify one or more treatment protocol units 120, he or she may access functionality that the transcranial magnetic stimulation application program code 122 provides to browse, select and edit a data structure that represents a treatment protocol unit 120. More generally, a treatment protocol unit 120 defines the manner in which one (and more typically at least two) or more magnetic assembly devices 104 are energized to create electric fields across various areas of the brain of a patient over a window of time. Such information is used by the transcranial magnetic stimulation application program code 122 to instruct the processor as to the manner in which to energize, via the controller 108, the set of magnetic assembly devices 104 to create such a field.

The one or more treatment protocol units 120 that the processor 112 executes under control of the transcranial magnetic stimulation application program code 122 provide commands to the controller 108 as to the manner in which it should instruct individual magnetic assembly devices 104 to rotate. Receipt of such signals from the controller 108 by a given magnetic assembly device 104 causes its actuator to rotate its associated magnet at a particular frequency for a particular duration. Such rotation of the magnet at a set frequency results in the generation of a desired electric field within the brain, which may be used as part of a therapy, diagnosis, mapping or other medical diagnostic treatment.

Advantageously, the transcranial magnetic stimulation application program code 122 allows the user to select sets of treatment protocol units to form one or more treatment protocols. Through the use of a user interface that the transcranial magnetic stimulation application program code 122 provides, which may be a GUI or text based interface, the user can define a set of treatment protocol units that the processor applies to the patient as a set treatment protocol. According to one embodiment, the transcranial magnetic stimulation application program code 122 serially applies the treatment protocol units comprising a treatment protocol. Alternatively, the transcranial magnetic stimulation application program code 122 may dynamically arrange and apply the treatment protocol units comprising a given treatment protocol. Sill further, the processor may execute and apply certain treat protocol units in parallel, e.g., at the same time. The user may also share treatment protocols and treatment protocol units with other users on other control devices by way of a network that the control device accesses via its network interface 110, which may further comprise receiving the individual treatment protocol units comprising a received treatment protocol.

In one particular arrangement, the transcranial magnetic stimulation application program code 122 instructs the processor 112 of the control device 106 to assemble the treatment protocol units 120 into a treatment protocol to apply a treatment that implicates one or more particular magnetic assembly devices 104. In an alternative arrangement, the transcranial magnetic stimulation application program code 122 instructs the processor 112 to assemble the treatment protocol units 120 into a general treatment program from a set of one or more treatment protocol units 120 used to control the energization of all of the magnetic assembly devices 104. In a further arrangement, the transcranial magnetic stimulation application program code 122 instructs the processor 112 to generate a plurality of magnetic assembly device specific treatment protocols from the treatment protocol units 120, each magnetic assembly device specific treatment protocol to be carried out by a specific magnetic assembly device 104, and a general treatment protocol that is carried out by the remaining non-specified magnetic assembly devices 104.

Building on the prior point, assume an exemplary treatment protocol having a pattern of treatment protocol units, the application of which is directed to the magnetic assembly device positioned in proximity to the Broca's Area of the patient. All other magnetic assembly devices use a similar treatment program, but substitute location dependent treatment protocol units. Since each of the treatment protocol units, when combined in a treatment protocol, are a representation of control or operational parameters for specific magnetic assembly devices, the processor executing the transcranial magnetic stimulation application program code can generate a single control signal for distribution by the controller that details the desired rotation frequencies, durations, quintessence periods or other conditions for each of the magnetic assemblies. In other words, the user can select a treatment protocol and cause the system to implement a treatment, diagnosis, mapping and so on by implementing the pattern of treatment protocol units, in parallel or serial, all based on the selection of a particular treatment protocol.

Figure 3:
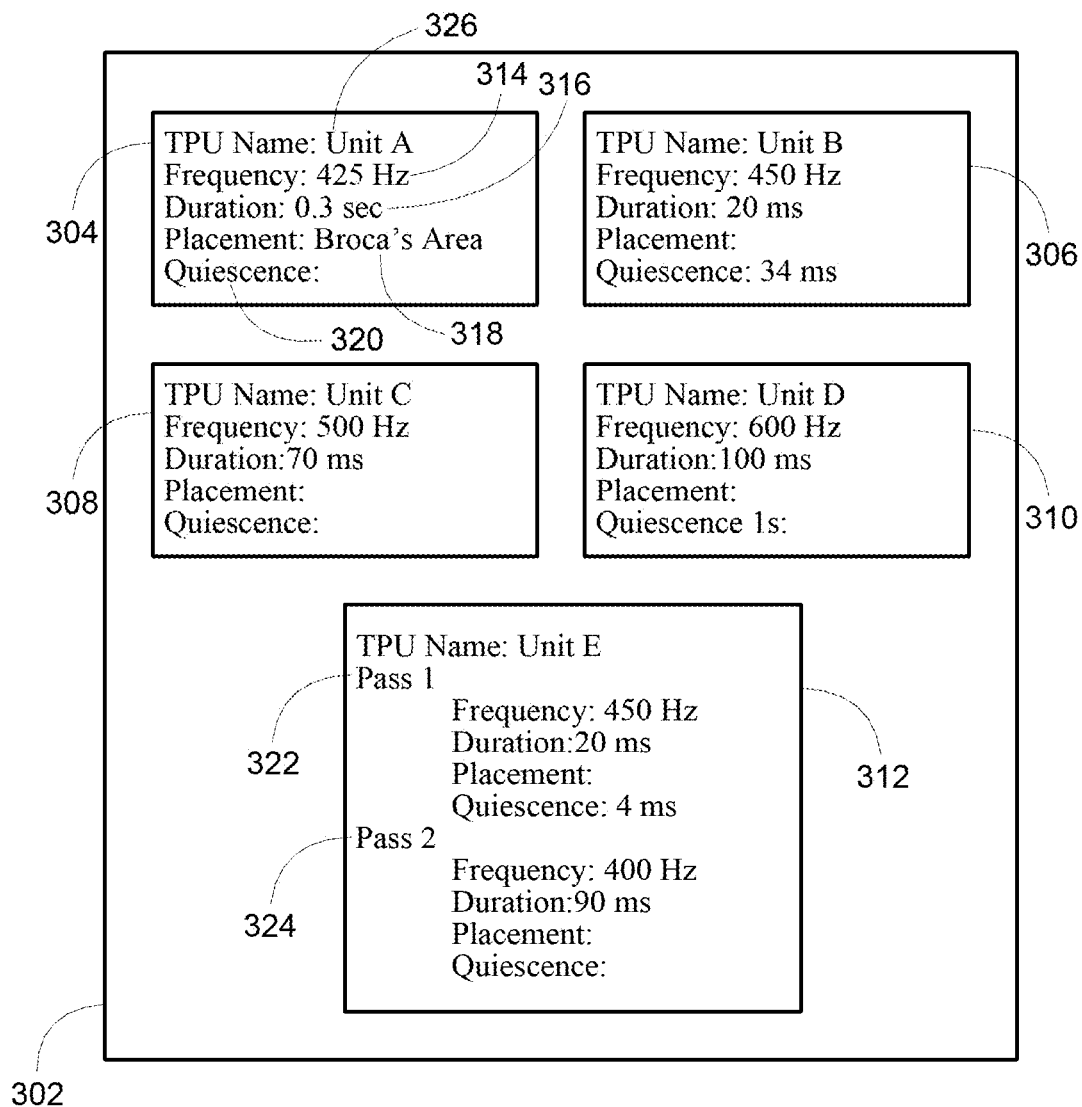
FIG. 3 presents a block diagram illustrating a persistent data store maintaining a set of treatment protocol units according to one embodiment of the present invention.

With reference now to FIG. 3, a given treatment protocol unit is represented as a data object which serves to provide structure to a set of data regarding a treatment protocol, such as but not limited to, rotation frequency, motor energization duration, quiescence period and specific energizing of a particular set of zero or more magnetic assembly devices. In accordance with the illustration of FIG. 3, a persistent data storage device 202, e.g., a hard disk drive, provides persistent storage for data representing discrete treatment protocol units ("TPU"): TPU A 304, TPU B 306, TPU C 308, TPU D 310 and TPU E 312. A given treatment protocol unit 304, 306, 308, 310 and 312 provides the control device with information that the processor can use to instruct the controller as to the transmission of specific electrical control signals to be sent to (or suppressed from) a given one of the magnetic assembly devices.

A given treatment protocol unit comprises a number of data points regarding the instructions that the TPU represents. In accordance with the embodiment that FIG. 3 illustrates, a given treatment protocol unit comprises: a name or label for the TPU 326, a frequency value 314 representing a rotational frequency for one or more magnetic assembly devices, a rotational duration 316, a placement area 318 for application of the treatment protocol unit and a quiescence period 320. Those of skill in the art recognize that a given TPU may identify values for less than all of the key-value pairs contained in a given TPU, e.g., some values can be null, and that the parameters represented in a given TPU can differ from those shown in the embodiment of FIG. 3. For example, treatment protocol unit B 306 comprises an active duration or period of 20 milliseconds, denoting an energized state of one or more magnetic assembly devices, and a quiescence period of 34 milliseconds, denoting the deactivation of the magnetic assembly devices during the quiescence period, with a rotational frequency of 450 Hertz. Alternatively but similarly, treatment protocol unit C 308 provides information with respect to rotational frequency and duration, but is silent regarding placement and any quiescence period. Thus, a given treatment protocol unit may comprise a sequence of individual active periods interspaced with specific quiescence sections. As will be understood, a quiescent period can be defined by a treatment protocol unit ("TPU"), without specifying a frequency or duration or placement, as a TPU defined in this manner can serve as a spacer between active TPUs that are combined to define a treatment protocol.

The described TPUs can also be used to implement a Theta Burst Stimulation (TBS) protocol. Here, the TBS protocol is defined as one or more active TPUs followed by a second, quiescent TPU. In one particular implementation, the active TPU(s) defines a three (3) pulse pattern delivered at a frequency of 50 Hz, each pulse lasting 20 ms. A quiescent TPU lasting 160 ms defines an inter-burst interval from the last burst of the present pattern to the first burst of the next pattern. The active and quiescent TPSs combined for a repeating treatment pattern of having a duration of 200 milliseconds. While a single TPU can define a multiple burst pattern, it is also envisioned that the active TPUs defines a single burst. Thus, a collection of single burst TPUs (each without a period of quiescence following the burst) followed by a single or collection of quiescent TPUs can also be used to define a TBS protocol.

In one or more implementations, a treatment protocol unit can issue a command to a single magnetic assembly device as in treatment protocol unit A. According to the operational parameters that treatment protocol unit A identifies, the protocol unit instructs that only the magnetic assembly device located a "Broca's Area" is to be energized. Similarly, a given treatment protocol unit may identify a set of one or more magnetic assembly devices on the basis of the location(s) of such magnetic device assembly on the cap, which energize for rotation over a period of time on the basis of the instructions in the given treatment protocol unit that the processor at the control device interprets. In another arrangement, the magnetic assembly device (MAD) can be addressable on the basis of its connection point to the cap, with the location of the magnetic device assembly being defined as a result of its connection to the cap by virtue of contacts on the cap. As a related matter, signal feedback between the cap concerning the operational capabilities/status of the MADs that are attached to the cap and their location of attachment can coordinate with the system so as to permit treatment protocols to be selected, and to inform the clinician or patient that additional or different MADs have to be attached and where they have to be attached before a particular treatment protocol is implemented.

As shown by way of treatment protocol unit E 212, a treatment protocol unit may comprise multiple, disparate periods or passes within a treatment protocol unit in which one or more magnetic assembly devices are variously energized. Continuing with exemplary treatment protocol unit E 212, the treatment protocol unit comprises a first and second energized periods, 222 and 224, respectively, lasting 20 milliseconds and 90 milliseconds, respectively, separated by a defined quiescence period that lasts for 4 milliseconds. Thus, a given treatment protocol unit may comprise complex multi-pass logic that energize one or more magnetic assembly devices in a pattern to achieve a particular purpose or usefulness. As will be appreciated, a particular treatment protocol can be defined by a set of one or more treatment protocol units, and invoked by selecting that particular treatment protocol.

As described above, a given treatment protocol unit identifies one or more particular key-value pairs that ultimately instruct a magnetic assembly device as to its operational state at a given point in time. Accordingly, a given treatment protocol unit need not define each key-value pair contained within a given treatment protocol unit, e.g., some keys can have a null or empty value. For example, a treatment protocol unit can provide information about a quintessence period free of any energization state information, e.g., frequency and duration values are set to null. In such a configuration, a quiescence only treatment protocol unit operates as a break or spacer in the active sessions of a treatment protocol. In this way, quiescence periods can be introduced to accompany treatment protocol units lacking a quiescence period. By way of example, treatment protocol units that only define a quiescence period can be used to ensure that there is a set repetition frequency of between 0.1 to 2 Hertz.

A given treatment protocol unit may be implemented by the processor that is executing transcranial magnetic stimulation application program code. Alternatively, or in conjunction with the foregoing, the transcranial magnetic stimulation application program code may instruct the processor to implement a treatment protocol that comprises a plurality of treatment protocol units. The transcranial magnetic stimulation application program code comprises program code to instruct the processor to present a user interface to a user or operator (e.g., a clinician) of the control device that will allow such an individual to select one or more treatment protocol units for inclusion in a treatment protocol.

Figure 4A:
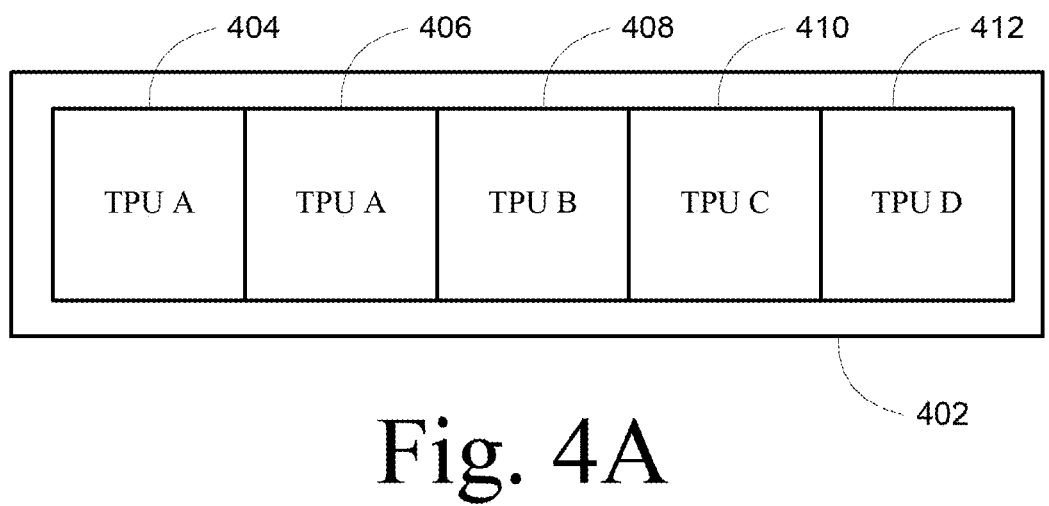
FIG. 4A presents a block diagram illustrating a treatment protocol that comprises multiple treatment protocol units in accordance with one embodiment of the present invention.
Figure 4B:
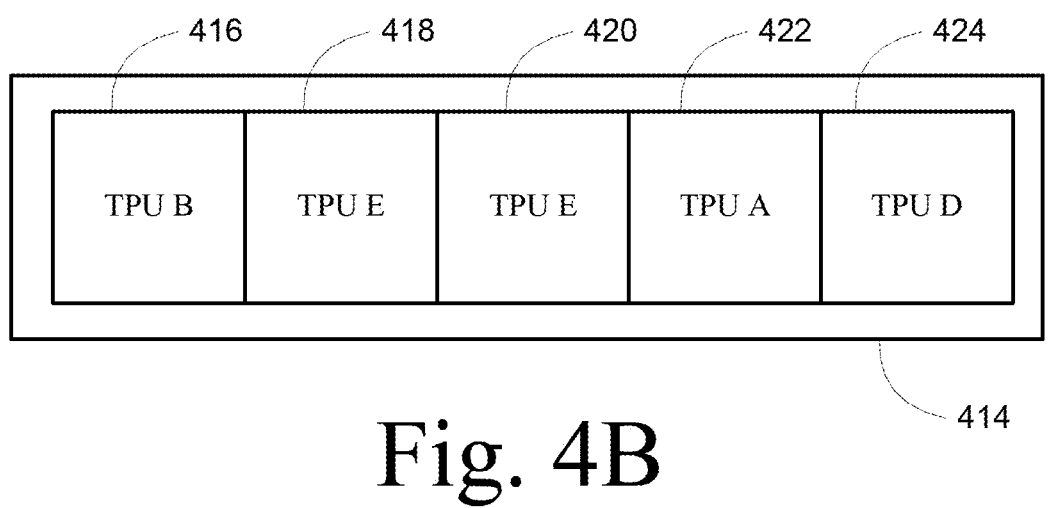
FIG. 4B presents a block diagram illustrating a treatment protocol that comprises multiple treatment protocol units in accordance with an alternative arrangement as compared to that of FIG. 4A.

As shown in FIG. 4A, upon selection of one or more desired treatment protocol units, the transcranial magnetic stimulation application program code according to one embodiment instructs the processor to assemble the treatment protocol units into a treatment protocol 402. As will be understood, a treatment protocol can comprise a stored selection of TPUs which can be selected for implementation. The transcranial magnetic stimulation application program code instructs the processor at the control device to assemble the individual treatment protocol units 404, 406, 408, 410 and 412 into a treatment protocol 402 that is suitable for treating a specific ailment or patient, or to load from storage and/or otherwise implement a stored treatment protocol. According to one embodiment, the transcranial magnetic stimulation application program code instructs the processor to configure or assemble a set of treatment protocol units 404, 406, 408, 410 and 412 according to an overall desired length of treatment. For example, if the desired treatment is two minutes, the transcranial magnetic stimulation application program code instructs the processor to assemble the treatment protocol units into a treatment protocol 402 that ensures the resulting treatment protocol is of the desired length, such as by looping the TPUs that comprise the treatment protocol until the treatment duration has been achieved. Alternatively, longer duration treatment protocol units can be used in a given treatment protocol in order to provide a treatment program of a desired length. Alternative embodiments contemplate assembly of treatment protocol units in an ad-hoc fashion to treat a desired illness or symptoms that a patient is experiencing, such as the arrangement of treatment protocol units 416, 418, 420, 422 and 424 to create the treatment protocol that FIG. 4B illustrates.

The resulting treatment protocol 402 or 414 is a data object containing data used to instruct all or a portion of the magnetic assembly devices to generate a specific series of electric fields within the brain of the patient. Where different magnetic assembly devices of the same cap have different treatment protocol units applied, a treatment program dataset is created, which may be saved in a persistent data store as a library of treatment protocols. Thus, a collection of treatment protocols are generated whereby different individual treatment protocols are used to control one or more specific magnetic assembly devices.

Figure 5:
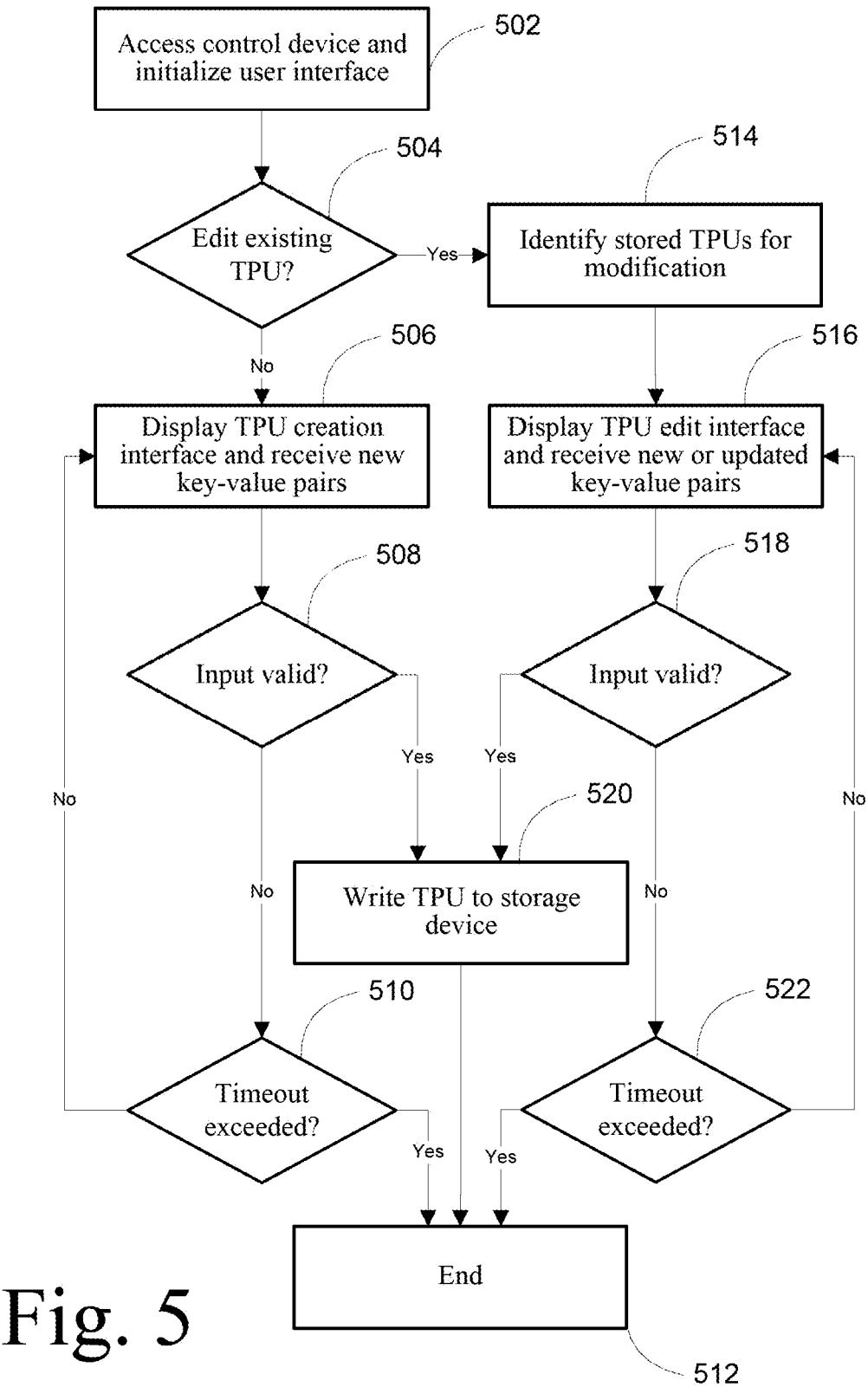
FIG. 5 presents a flow diagram illustrating a process for creating or modifying a treatment protocol unit in accordance with one embodiment of the present invention.
Figure 6:
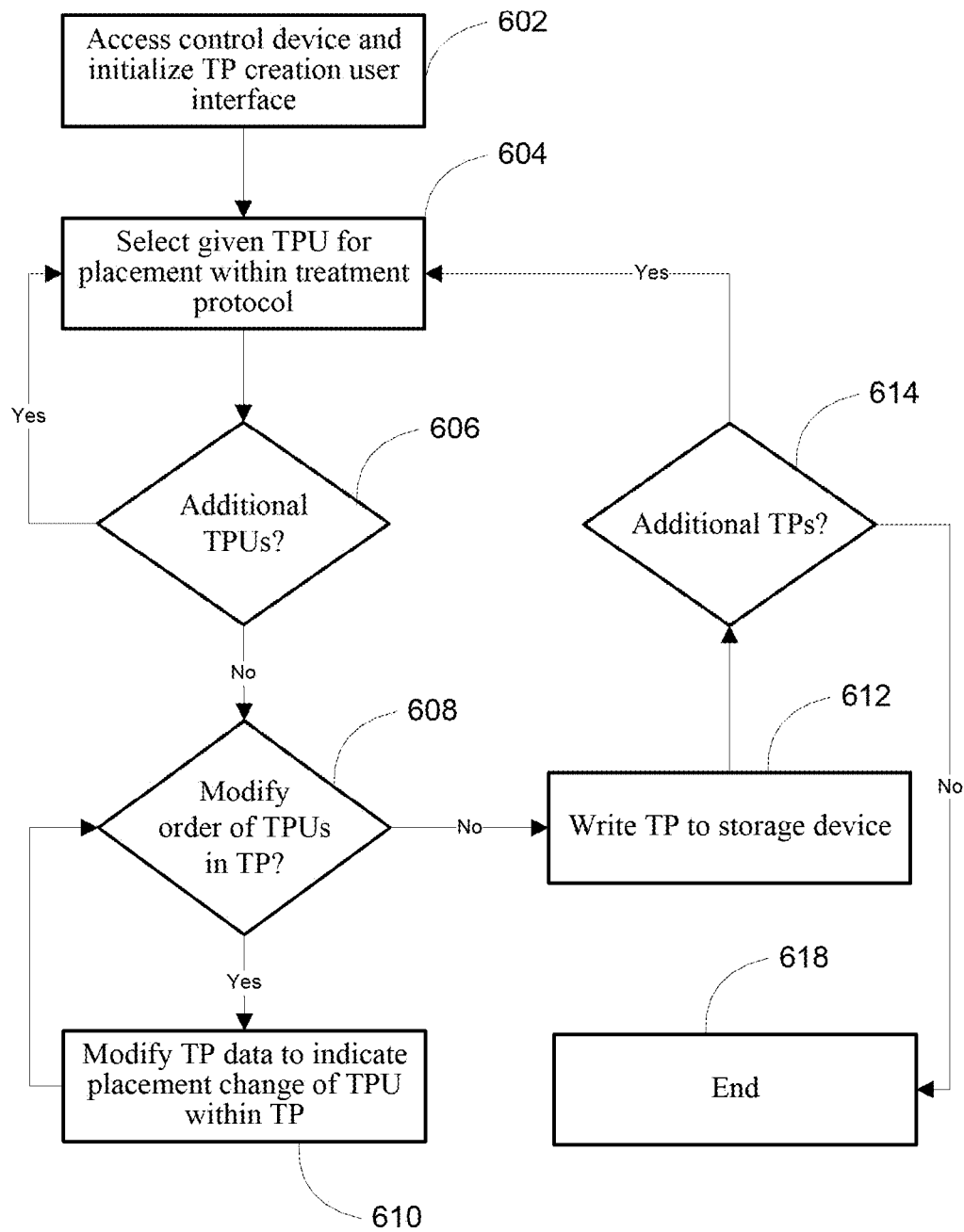
FIG. 6 presents a flow diagram illustrating a process for the creation of a new treatment protocol in accordance with one embodiment of the present invention.
Figure 7:
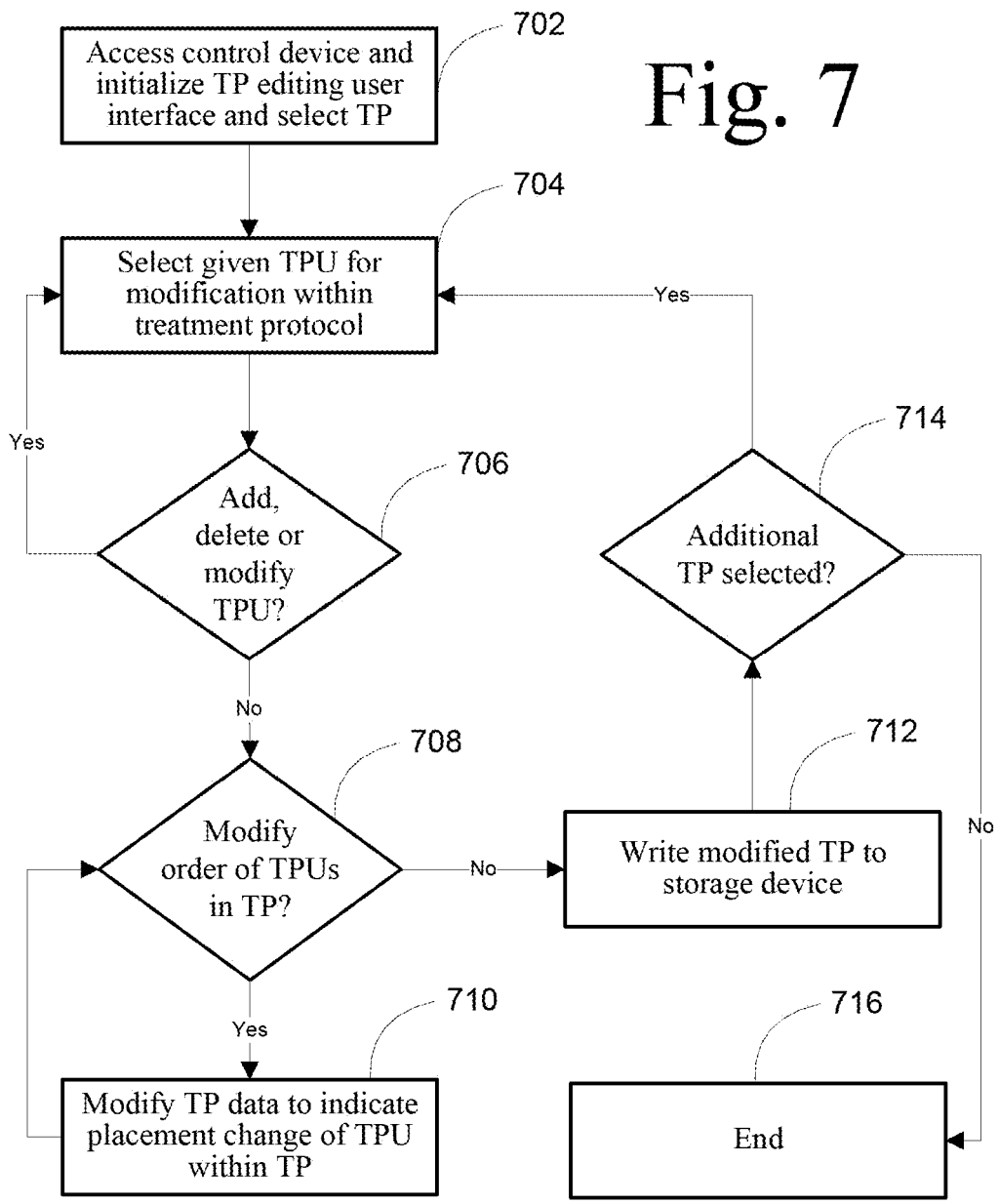
FIG. 7 presents a flow diagram illustrating a process for editing an existing treatment protocol in accordance with one embodiment of the present invention.

With particular reference to FIG. 5, the control device executes transcranial magnetic stimulation program code implemented as a collection of submodules (each composed of program code for execution by a processor) that configure the control device to communicate with a local or remote storage device, such as the persistent data store, RAM, ROM and network accessible data stores, to implement a transcranial magnetic stimulation treatment protocol. Furthermore, certain embodiments implement additional program code modules and submodules, such as authentication or validation programmatic routines, which are used to access the data and provide security or other credentials prior to accessing the stored data. The processor, when executing the transcranial magnetic stimulation program code, presents graphical user interface controls on a display device and allows the user to create and modify one or more of treatment protocol units, step 502. Those of skill in the art recognize that other user interfaces are applicable, including text-based "command line" interfaces. As will be appreciated, the flow diagram of FIG. 5 as well as those of FIGS. 6 and 7 are appropriate for certain clinicians and trained operators, but not for a user who is to wear the cap and undergo a treatment, diagnosis, or other session wearing the cap 102.

Through use of the user interface controls that the control device generates, a user provides a selection indicating a desire to create a new treatment protocol unit or edit an existing treatment protocol unit, step 504. The transcranial magnetic stimulation program code implements programmatic logic to fork program flow on the basis of the input that the user provides. Accordingly, where the user instructs the control device to create a new treatment protocol unit, step 504, the program code instructs the processor to display a treatment protocol unit creation interface that allows that user to supply key-value pairs identifying operational parameters of one or more magnetic assembly devices for execution by the control device as a treatment protocol unit, step 506. Certain embodiments provide that a treatment protocol unit identifies multiple energized periods, which the user may accordingly provide as a series of one or more key-value pairs for each period.

The user supplies the desired operational parameters as a set of key-value pairs that data acquisition routines of the transcranial magnetic stimulation program code attempt to validate as acceptable input, step 508. A number of thresholds may be evaluated to ensure that the operational parameters set by the key-value pairs not cause the device to operate in a manner that would be harmful to the patient, the user or both. If the input that the user provides is invalid, step 508, the program code instructs the processor to perform a timeout check to determine if the user has exceeded an acceptable number of attempts to provide valid input, step 510. Where the check at steps 508 and 510 both evaluate to false, program flow returns to step 506 with the program code instructing the processor to display the treatment protocol unit creation interface that allows that user to supply key-value pairs identifying operational parameters for execution by the control device as a treatment protocol unit. Where the processor determines that the input is valid, the processor opens a communication channel to the persistent storage device and issues a write command to store the newly created treatment protocol unit, step 520, and the process concludes, step 512. As will be appreciated, the threshold can be preset as a function of the treatment type (e.g., higher thresholds for depression treatment than, say, for mood modification).

Returning to step 504, if the user instructs the control device to edit or modify an existing new treatment protocol unit, then the program code instructs the processor to display a listing of available treatment protocol units, which may be stored locally, e.g., on the persistent storage device at the control device, or remotely for access via the network interface of the control device, step 514. The user selects a given treatment protocol unit for modification from the set of available treatment protocol units and the program code instructs the processor to display a treatment protocol unit edit interface that allows that user to edit existing or supply new key-value pairs that identify operational parameters for execution by the control device, step 516.

The user supplies the desired operational parameters as a set of key-value pairs that data acquisition routines of the transcranial magnetic stimulation program code attempt to validate as acceptable input, step 518. A number of thresholds may be evaluated to ensure that the operational parameters set by the key-value pairs not cause the device to operate in a manner that would be harmful to the patient, the user or both. If the input that the user provides is invalid, step 518, the program code instructs the processor to perform a timeout check to determine if the user has exceeded an acceptable number of attempts to provide valid input, 522. Where the check at steps 518 and 522 both evaluate to false, program flow returns to step 516 with the program code instructing the processor to display the treatment protocol unit edit interface that allows that user to modify existing or supply new key-value pairs that identify operational parameters for execution by the control device. Where the processor determines that the input is valid, the processor opens a communication channel to the persistent storage device and issues a write command to store the modified treatment protocol unit, step 520, and the process concludes, step 512.

In addition to providing tools that allow for the creation and modification of treatment protocol units, transcranial magnetic stimulation software in accordance with embodiments of the present invention provides programmatic routines for the creation of treatment protocols consisting of a plurality of treatment protocol units. According to the embodiment set forth in FIG. 6, the process of creating a new treatment protocol comprises accessing the control device to instantiate and initialize the treatment protocol creation user interface, step 602.

The treatment protocol creation user interface provides the user with controls to browse a set of treatment protocol units that the control device can maintain on local storage, remote storage, or various combinations thereof. Using this user interface, the user selects a given treatment protocol unit for inclusion as part of the newly created treatment protocol, step 604. The program code instructs the processor to perform a check to determine if there are additional treatment protocol units for inclusion in the new treatment protocol, step 606. Upon receipt of feedback indicating that there are additional treatment protocol units for inclusion in the new treatment protocol, program flow returns to step 604 with the user interface allowing the user to select an additional treatment protocol unit, or similarly, remove a selected treatment protocol unit.

Where the user indicates that there are no additional treatment protocol units to add to or remote from the newly created treatment protocol, step 606, the program code instructs the processor to perform a check to determine if there is to be a modification of the order of the treatment protocol units selected to be part of the treatment protocol, as indicated at step 608. Where the check evaluates to true, program code instructs the processor to modify the treatment protocol creation user interface so as to provide the user with controls to modify the treatment protocol data to indicate a placement change of treatment protocol units within the treatment protocol, step 610. Accordingly, the control device executes the treatment protocol in the modified order at runtime.

After the check at step 608 evaluates to false, thereby indicating completion of any further modification to the treatment protocol data, the control device writes the treatment protocol data to a data storage device, step 612, which may be a persistent data storage device. Where the data storage device is remote from the control device, program code instructs the processor to open a network connection to the remote data store for transmission and storage thereupon. The program code instructs the processor to perform a further check to determine if there are additional treatment protocols for creation, step 614, directing program flow back to step 604 where the check evaluates to true. Where there are no further treatment protocols that require creation, program flow terminates, step 618, and control returns from the subroutine to a master control component of the transcranial magnetic stimulation program code.

FIG. 7 illustrates one embodiment of a process for modifying an existing treatment protocol, which comprises accessing the control device to instantiate and initialize the treatment protocol editing user interface, step 702. The treatment protocol editing user interface provides the user with controls to browse a set of treatment protocols that the control device may maintain on local storage, remote storage, or various combinations thereof. Using this user interface, which may be a graphical user interface, the user selects a given treatment protocol for modification, as well as a specific treatment protocol unit for modification, step 704. The program code instructs the processor to perform a check to determine if an attempt is being made to add, modify or delete a treatment protocol unit in accordance with the treatment protocol under consideration, step 706.

Upon execution of the command by the processor and recording the update to the treatment protocol unit, program flow loops through steps 704 and 706 to allow the user to add, delete or modify additional treatment protocol units that are part of the treatment protocol under consideration, substantially as described above in connection with FIG. 5. The graphical user interface that the processor presents under the control of the program code provides an access to programmatic controls that allow for execution of such control commands and data updates.

Where the user indicates that there are no additional treatment protocol units to add, delete or modify from the treatment protocol, step 706, the program code instructs the processor to perform a check to determine if there is to be a modification of the order of the treatment protocol units selected to be part of the treatment protocol. Where the check evaluates to true, program code instructs the processor to modify the treatment protocol creation user interface so as to provide the user with controls to modify the treatment protocol data to indicate a placement change or treatment protocol units within the treatment protocol, step 710. Accordingly, the control device executes the treatment protocol in the modified order at runtime.

After the check at step 708 evaluates to false, thereby indicating completion of any further modification to the treatment protocol data, the control device writes the treatment protocol data to a data storage device, step 712, which may be a persistent data storage device. Where the data storage device is remote from the control device, program code instructs the processor to open a network connection to the remote data store for transmission and storage thereupon. The stored modified treatment protocol unit can be stored as a standalone unit without overwriting the TPU that was just modified, or, if the modified TPU was part of a previously stored treatment protocol, the user can select to have the write command store the modified treatment protocol unit as part of a modified version of the previously stored treatment protocol, again without overwriting the treatment protocol that was just modified.

The program code instructs the processor to perform a further check to determine if there are additional treatment protocols for editing, step 714, directing program flow back to step 704 where the check evaluates to true. Where there are no further treatment protocols that require editing, program flow terminates, step 718, and control returns from the subroutine to a master control component of the transcranial magnetic stimulation program code.

Figure 8:
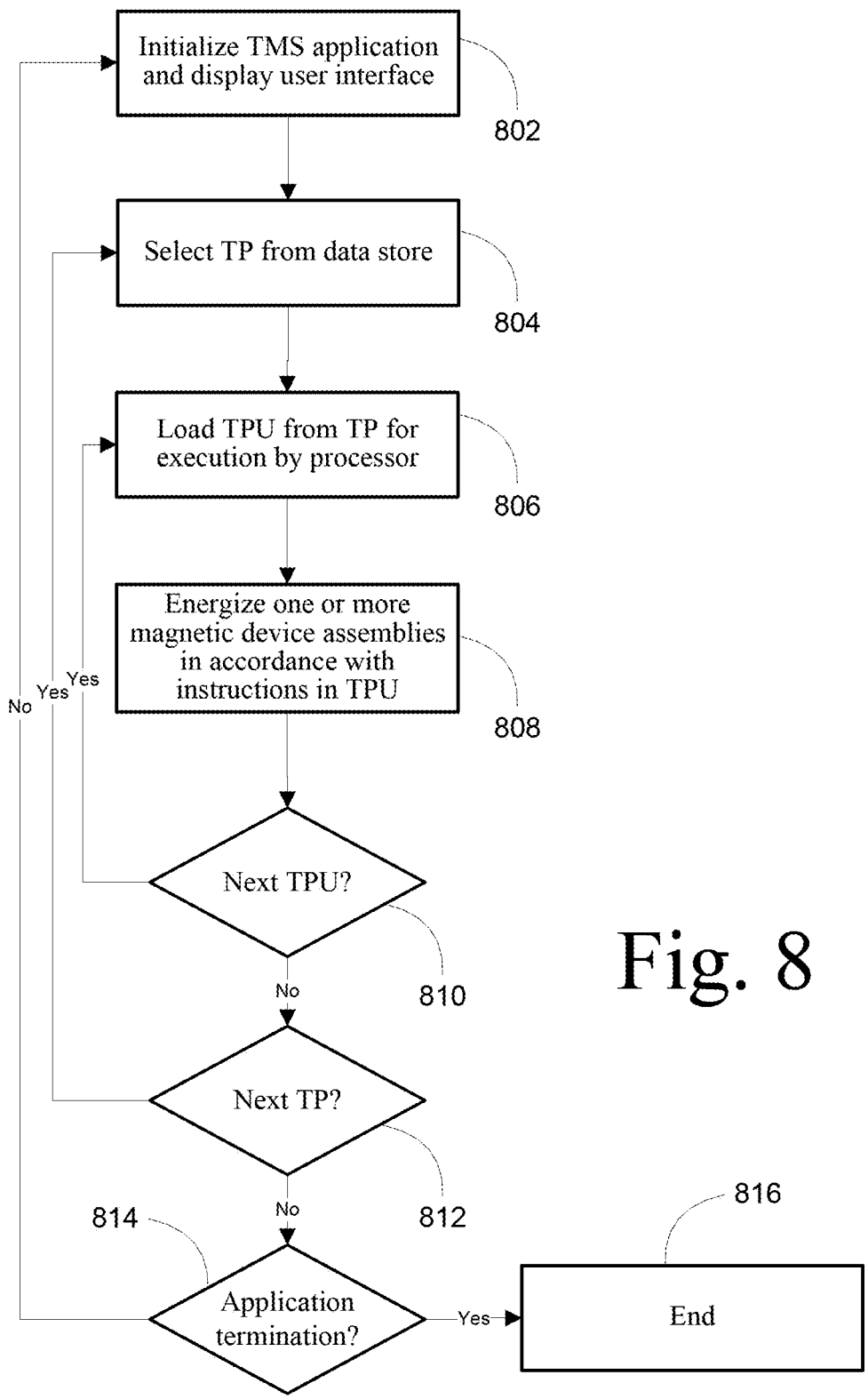
FIG. 8 presents a flow diagram illustrating a process for executing a transcranial magnetic stimulation treatment protocol on a patient in accordance with one embodiment of the present invention.

As described throughout, the processor at the control device executes the transcranial magnetic stimulation program code to variably energize one (and more typically two) or more magnetic assembly devices spaced on the cap 102 at locations that span at least a portion of the cranium of a patient. FIG. 8 illustrates one embodiment of a method to effect such transcranial magnetic stimulation. The method of FIG. 8 begins with the initialization of a transcranial magnetic stimulation subroutine that is embodied as program code deployed to the control device as part of the transcranial magnetic stimulation program code. Execution of the subroutine by the processor causes an attached display device to present a stimulation specific user interface, step 802, which may be a graphical user interface or other interface suitable to convey information in accordance with the various embodiments of the invention.

The control device provides programmatic tools allow for the selection of one or more treatment protocols, step 804, e.g., through interaction with the interface that the processor presents on the display device. The control device may provide access to treatment protocols from local storage, as well as treatment protocols on remote data stores. According to one embodiment, the control device accesses a remote data store via a network through use of a network interface. Upon connection to the remote data store, the control device copies the transaction protocol to local storage for execution by the processor. Alternatively, the control device accesses the remote data store and reads transaction protocol information as needed, e.g., remote execution of the data.

The selection of one or more treatment protocols for application to a patient, step 804, may comprise presenting a user with a listing of available treatment protocols, which may also comprise a listing of the individual treatment protocol units making up a given treatment protocol. Selection of a given treatment protocol can be made on the basis of applying a treatment directed towards a particular ailment. For example, a drop down menu is provided in one embodiment by a graphical user interface that lists a set of exemplary potential ailments that require treatment: depression, neurological and psychiatric disorders, migraines, aphasia, anxiety, Parkinson's disease, tinnitus, autism, schizophrenia, Alzheimer's, ALS, stroke (e.g. ischemic), Myotonic Dystrophy type 1 (DM1), stuttering, epilepsy, Parkinson's disease, visceral pain and dystonia, cocaine, opioid and other addictive behaviors. A user can select a treatment protocol (comprising one or more treatment protocol units) that has been previously designed, and potentially verified, to ameliorate such conditions. Alternatively, the user is free to select one or more treatment protocol units depending on specific conditions or circumstances, for example, one or more collections of treatment protocol units may be presented as having applicability to a particular ailment, such as addiction or pain. The data store that maintains the treatment protocols and/or treatment protocol units can by associated with metadata that functions as a suggestion as to the applicability of a given treatment protocol unit or treatment protocol.

Optionally, information can be received from a patient database concerning the patient who is to wear the cap 102 over the network interface 110 which can define (e.g., constrain) the selection of treatment protocols to those that correspond to a prescription by a clinician or other health care provider. Optionally, the set of treatment protocols available for selection can be defined (e.g., constrained) as a function of prior treatments. For instance, a treatment protocol can comprise a regimen of treatments in which the duration, energy, or other parameters are established for a patient, yet which vary over the course of treatment. In this way, a predefined regimen of treatment can be implemented (and repeated with the same or other patients) with precision by virtue of providing a series of treatment protocols through a predefined regimen.

More generally, as will be understood from the foregoing description, a given treatment protocol comprises one or more treatment protocol units; a given treatment protocol unit contains instructions that identify the operational parameters of one or more magnetic device assemblies that are in communication with the control device executing software on its processor to interpret such instructions. The user or an automated software process selects a given treatment protocol from a set of available treatment protocols, step 804, or may select one or more treatment protocol units for application as a treatment protocol. In response to receipt of a selection of a treatment protocol, the processor retrieves the treatment protocol units that the treatment protocol identifies into memory, e.g., RAM, for execution by the processor that is running the transcranial magnetic stimulation program code. According to one embodiment, the processor retrieves and loads treatment protocol units serially for execution. Alternatively, the processor may retrieve multiple treatment protocol units that it loads into working memory for serial or dynamic execution, which depends on specific instructions contained in the treatment protocol unit, the transcranial magnetic stimulation program code or various combinations thereof.

Upon receipt of a signal to begin a treatment protocol, the processor under the control of the transcranial magnetic stimulation program code retrieves a first treatment protocol unit for execution, step 806. Upon execution of the treatment protocol unit, the processor issues instructions in accordance with the treatment protocol unit to specific magnetic assembly devices that causes the motor or other actuator within a given magnetic assembly device to energize and induce the desired electrical fields within the brain of the wearer, step 808. In one embodiment, the processor passes instructions regarding the energizing of specific magnetic assembly devices to the controller. The controller parses or translates the treatment program into control signals or identifies the operational parameters to implement for some or all of the magnetic assembly devices. For example, the controller may close a switch that controls the magnet for a given duration and adjust a potentiometer (or its digital equivalent, e.g., a shift register) to select a desired rotation frequency. Alternatively, the processor at the control device communicates with each of the magnetic assembly devices directly and passes a control signal that causes the motor(s) to energize in accordance with instructions in a given treatment protocol unit.

According to certain embodiments, the control device is operative to modify one or more treatment protocol units to suit the needs of a patient, in order to define a particular treatment protocol, to bring the device within safe operating parameters, etc. Such modification according to one embodiment is in response to data that the control devices receives from one or more sensors that are deployed as part of a given magnetic device assembly. Program code that is part of the transcranial magnetic stimulation program code modifies the data values of one or more treatment protocol units, e.g., so as to alter duration, frequency or quiescence period. Similarly, such program code can dynamically reorder the sequence in which the processor applies a set of treatment protocol units, which can be based on feedback that the control device receives from one or more sensors or from the patient himself or herself. The processor executes the modified treatment protocol unit and or can store the modified treatment protocol unit prior or subsequent to execution. In a further implementation, based on feedback from the user, such a modified treatment protocol unit is uploaded or transmitted back to the database for dissemination to the user community. Furthermore, the uploaded modified treatment can be accompanied by feedback metadata obtained from the sensors integral to the magnetic assembly device or cap.

After execution of a treatment protocol unit by the processor, which may be accomplished in conjunction with the controller—in addition to other software and hardware components of the control device, the program code instructs the processor to perform a check to determine if a subsequent treatment protocol unit requires execution, step 810. Where additional treatment protocol units are present that require execution by the processor and application to the patent, program flow returns to step 806 with the processor loading a subsequent treatment protocol unit from memory that is part of the treatment protocol that the control device is applying to the patient. Where there are no additional treatment protocol units for application to the patient, the program code instructs the processor to determine if a subsequent treatment protocol requires execution, step 812. Where additional treatment protocols are present that require execution by the processor and application to the patent, program flow returns to step 804 whereby the user or an automated software process selects a given treatment protocol from a set of available treatment protocols (or individual treatment protocol units for application to a patient). If there are no additional treatment protocol units or treatment protocols that require application to the patient, the program code instructs the processor to perform a check to determine if the application is terminated, step 816. Application termination causes the process of FIG. 8 to conclude, step 716; otherwise the application enters a wait state with the display of the application user interface, step 802.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems are cited throughout this application, the disclosures of which are incorporated herein by reference. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those points, and by equivalents of such features.

I claim:

1. A transcranial magnetic stimulation ("TMS") device for use with a patient comprising:
  a head mount for disposition on a head of the patient and configured with a plurality of attachment points;
  a plurality of magnetic assembly devices connected to respective ones of the plurality of attachment points, each magnetic assembly device being configured with an actuator device to actuate a magnet and being configured to receive a control signal addressed to the given magnetic assembly device;
  a memory; and
  a processor configured by program code executed thereby to:
    generate one or more treatment protocol units, by assembling a series of key-value pairs into a data structure, wherein data values of the data structure are used to instruct all or a portion of the magnetic assembly devices to generate a specific series of electric fields within a brain of the patient corresponding to one or more operational parameters for the plurality of magnetic assembly devices,
    validate the generated one or more treatment protocol units against threshold value for at least one of the series of key-values pairs;
    generate a control signal using at least information contained in two or more validated generated treatment protocol units,
    energize at least one of the plurality of magnetic assembly devices over a period of time to cause the magnet to actuate according to the control signal, and monitor a response by the patient to energizing the respective actuators of the plurality of magnetic assembly devices.

2. The TMS device of claim 1 wherein the plurality of magnetic assembly devices are permanently attached to the head mount.

3. The TMS device of claim 1 wherein the plurality of magnetic assembly devices are attached to the head mount in a releasable manner.

4. The TMS device of claim 1, wherein the processor is configured to modify at least one of the treatment protocol units prior to transmission of the control signal.

5. The TMS device of claim 1 wherein at least one of the data values of the one or more generated treatment protocol units indicates a period of time having a duration from 1-100 milliseconds and at least one other data value indicates repetition rate of 0.1 to 2 Hertz.

6. The TMS device of claim 1 wherein the given magnetic assembly device comprises a magnet for selectively providing a rapidly changing magnetic field of at least 500-600 tesla/second corresponding to a magnet movement speed of no less than 400 hertz.

7. The TMS device of claim 1 comprising one or more sensors that monitor one or more operational parameters of the given magnetic assembly device.

8. The TMS device of claim 7 where the one or more sensors are selected from the set consisting of at least a temperature sensor, a magnetometer, and an electrode.

9. The TMS device of claim 1, wherein the control signal is generated by assembling at least one of the one or more generated treatment protocol units in order to provide a treatment protocol.

10. The TMS device of claim 9, wherein the treatment protocol comprises a data object containing data used to instruct all or a portion of the magnetic assembly devices to generate the specific series of electric fields within the brain of the patient.

11. The TMS method of claim 9, wherein the treatment protocol comprises a data object containing data used to instruct all or a portion of the magnetic assembly devices to generate the specific series of electric fields within the brain of the patient, and wherein the control signal is received by retrieval of the data object from a persistent data storage device.

12. The TMS device of claim 1, wherein the processor is further configured by program code to assemble the one or more treatment protocol units according to an overall length of treatment.

13. The TMS device of claim 12, wherein the processor is configured by program code to loop the one or more treatment protocol units to increase the overall length of treatment.

14. The TMS device of claim 12, wherein the processor is configured by program code to execute longer duration treatment protocol units that comprise a treatment protocol to increase the overall length of treatment.

15. A method for providing Transcranial Magnetic Stimulation ("TMS") to a patient, the method comprising:
providing a head mount for disposition on a head of a patient, the head mount comprising a plurality of points for releasably mounting a plurality of magnetic device assemblies, each magnetic device assembly comprising a magnet and an actuator device for selectively providing a rapidly changing magnetic field capable of inducing weak electric currents in a brain of the patient so as to apply a treatment that modifies natural electrical activity of the brain of the patient;
positioning the head mount on the head of the patient in conjunction with a selected number of the plurality of magnetic device assemblies on the head mount at selected locations;
generating one or more treatment protocol units, by assembling a series of key-value pairs into a data structure held in a memory of a processor, wherein data values of the data structure are used to instruct all or a portion of the magnetic assembly devices to generate a specific series of electric fields within the brain of the patient corresponding to one or more operational parameters for the plurality of magnetic assembly devices;
validating the generated one or more treatment protocol units against threshold value for at least one of the series of key-values pairs;
assembling two or more validated treatment protocol units into a treatment protocol for execution by a programmable processor, the programmable processor operative to generate a control signal utilizing the two or more validated treatment protocol units; and
providing a rapidly changing magnetic field with at least one of the magnet assemblies in accordance with the treatment protocol and in response to receipt of the control signal.

16. The TMS method of claim 15 comprising modifying at least one of the one or more generated treatment protocol units upon a determination that the generated treatment protocol unit is invalid.

17. The TMS method of claim 15, wherein the treatment is selected from depression, neurological and psychiatric disorders, migraines, aphasia, anxiety, Parkinson's disease, tinnitus, autism, schizophrenia, Alzheimer's, ALS, stroke, Myotonic Dystrophy type 1 (DM1), stuttering, epilepsy, Parkinson's disease, visceral pain and dystonia, cocaine, opioid and other addictive behavior.

18. A transcranial magnetic stimulation ("TMS") system comprising:
a plurality of magnetic assembly devices for deployment around a cranium of a patient, each of the plurality of magnetic assembly devices having at least one magnet and being configured to rotate the at least one magnet at one of a specific frequency or frequencies in response to receipt of a control signal addressed to at least one of the plurality of magnetic assembly devices and monitor, through one or more sensors, one or more operational parameters associated with the plurality of magnetic assembly devices; and
a processor in communication with a memory and configured by program code executing thereon to:
generate one or more treatment protocol units, by assembling a series of key-value pairs into a data structure, wherein data values of the data structure are used to instruct all or a portion of the magnetic assembly devices to generate a series of electric fields within a brain of the patient corresponding to one or more operational parameters of the magnetic assembly devices wherein a given generated treatment protocol unit identifies data corresponding to at least a rotational frequency,
validate the generated one or more treatment protocol units against threshold value for at least one of the series of key-values pairs,
generate a control signal using at least information contained in at least two generated treatment protocol units, energize at least one of the plurality of magnetic assembly devices over a period of time to cause the at least one of the magnet of the at least one of the plurality of magnetic assembly to actuate according to the control signal, and monitor the patient in response to energizing at least one of the plurality of magnetic assembly devices.

19. The TMS system of claim 18, wherein the control signal is generated by assembling the retrieved treatment protocol units in order to provide at least one treatment protocol.

* * * * *